United States Patent [19]

Clifford

[11] 4,204,996
[45] May 27, 1980

[54] PREPARATION OF O,O-DIALKYL PHTHALIMIDO-PHOSPHONOTHIOATE

[75] Inventor: David P. Clifford, Kings Lynn, England

[73] Assignee: Dow Chemical Company Limited, London, England

[21] Appl. No.: 957,115

[22] Filed: Nov. 2, 1978

[51] Int. Cl.$^2$ .......................................... C07D 209/48
[52] U.S. Cl. .............................................. 260/326 E
[58] Field of Search .................. 260/326 E, 326.5 FM

[56] References Cited

U.S. PATENT DOCUMENTS

| | | | |
|---|---|---|---|
| 3,336,419 | 8/1967 | Tolkmith | 260/326 E |
| 3,399,213 | 8/1968 | Osborne | 260/326 |
| 3,450,713 | 6/1969 | Tolkmith et al. | 260/326 E |
| 3,803,038 | 4/1974 | Olszewski | 260/326 E |
| 3,803,167 | 4/1974 | Senkbeil | 260/326 E |
| 3,853,909 | 12/1974 | Senkbeil | 260/326 E |

FOREIGN PATENT DOCUMENTS 1034493   6/1966   United Kingdom .

Primary Examiner—Donald G. Daus
Assistant Examiner—M. C. Eakin

[57] ABSTRACT

The present invention is directed to an improved method for preparing O,O-dialkyl phthalimidophosphonothioate (hereinafter alternatively referred to as "phosphonothioate"), corresponding to the formula

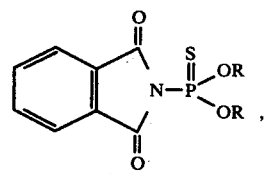

wherein each R is independently an alkyl group having from 1 to 4 carbon atoms, comprising reacting O,O-dialkyl phosphoramidothioate with phthalic anhydride in the presence of a tertiary amine catalyst.

15 Claims, No Drawings

PREPARATION OF O,O-DIALKYL PHTHALIMIDO-PHOSPHONOTHIOATE

BACKGROUND OF THE INVENTION

O,O-diethyl phthalimidophosphonothioate, methods for its preparation, and teachings of its utility as a pesticide and as an active toxicant in compositions for the control of insect, mite, helminth, plant fungal and bacterial organisms are described in U.S. Pat. Nos. 3,336,188; 3,450,713; 3,803,167; and 3,853,909. The method taught by the first two of the above patents basically entails the reaction of an N-alkali metal phthalimide with O,O-diethyl phthalimidophosphonothioate in the presence of an inert amido reaction medium such as, for example, N-methyl-2-pyrrolidone, dimethylformamide, hexamethylphsophoramide, N-acetylmorpholine and dimethylacetamide.

U.S. Pat. No. 3,803,167 teaches another method of preparing O,O-diethyl phthalimidophosphonothioate wherein O,O-diethyl phosphorochloridothioate is reacted with N-alkali metal phthalimide in the presence of an aromatic tertiary amine catalyst, such as pyridine, alpha-picoline, dimethylaniline, triphenylamine, pyrazine and quinoline, and a tertiary alcohol as solvent or reaction medium. Aliphatic tertiary amines were not found to be useful as catalysts in the process of U.S. Pat. No. 3,803,167.

U.S. Pat. No. 3,853,909 teaches preparing O,O-diethyl phthalimidophosphonothioate by reacting O,O-diethyl phosphonochloridothioate N-alkali metal phthalimide in the presence of a catalytic amount of 1,4-diazabicyclo-(2,2,2)octane and an inert tertiary alcohol as a solvent or reaction medium.

U.S. Pat. No. 3,399,213 teaches several methods of preparing O,O-diethyl phthalimidophosphonothioate. In one method, O,O-diethyl phosphoramidothioate is reacted with phthalic anhydride in the presence of dimethylformamide reaction medium and sodium hydride under a nitrogen atmosphere.

The above-described processes effectively produce the desired phosphonothioates. However, the process of the present invention is desirable in that it utilizes readily available starting materials while producing the desired phosphonothioate in good yields. The present process is particularly advantageous over the process described in U.S. Pat. No. 3,399,213 because the sodium hydride, which is hazardous, difficult to handle and nonrecoverable is replaced by a tertiary amine catalyst which is recoverable, easily handled, and less hazardous than sodium hydride.

DETAILED DESCRIPTION OF THE INVENTION

In accordance with the present invention, the desired phosphonothioate can be produced in high yields via a novel process which comprises reacting phthalic anhydride

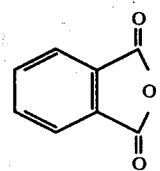

with an O,O-dialkyl phosphoramidothioate of the formula

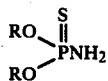

in the presence of a catalytic amount of at least one tertiary amine, said amine being an aliphatic tertiary amine of the formula NR$_3$ or a cyclic tertiary amine of the formula (CH$_2$)$_n$ N—R, where n is 4,5 or 6, and R in each of the above formula independently represents an alkyl group having from 1 to 4 carbon atoms, thereby to produce a dialkyl phthalimidophosphonothioate.

The phthalic anhydride may be substituted such that it carries a substituent in the cyclic dicarboximido radical such as described in British Patent Specification No. 1,034,493. The term "a phthalic anhydride" as used in the specification and claims refers to both unsubstituted phthalic anhydride and phthalic anhydride substituted as specified above. It is preferred, however, that the phthalic anhydride is unsubstituted. It is also preferred that the alkyl groups of the O,O-dialkyl phosphoramidothioate be ethyl groups, as this compound has exceptional activity in the control of fungi and similar applications.

It is generally preferred to carry out the reaction of the method of this invention without the use of a solvent although the reaction can fully be run in the presence of an alkane or lower haloalkane (i.e. a haloalkane having up to 4 or 6 carbon atoms) or reaction medium.

An essential feature of the present process is the utilization of the amine catalysts that are specified herein. The absence of such catalysts will drastically reduce the yield of the desired phosphonothioate. Examples of suitable aliphatic tertiary amine catalysts for use herein are triethylamine, trimethylamine, and tributylamine. The preferred tertiary amine catalyst is triethylamine. The preferred cyclic tertiary amine is N-ethylpiperidine. Other catalysts which are suitable for use in the process of the present invention are N-ethylpyrrolidine and hexamethylene imine. As a class, amines of the formula NR$_3$, wherein R is as defined above, are preferred. The most preferred catalyst is triethylamine.

In the present specification and claims, the definition for the term R encompasses both straight or branched chain alkyl groups.

As indicated above, the formation of the desired phosphonothioate will take place via the claimed process when a solvent is not employed, and therefore, a solvent should not be considered to be a critical element in the present process. However, when employing a solvent, the preferred solvents for use in the present invention are those which have a low dielectric constant. In particular, lower cyclic and non-cyclic alkane and lower haloalkane solvents such as cyclohexane, hexane, decane, and dichloroethane are preferred. The most preferred solvent is hexane. The terms "lower cyclic and non-cyclic alkane" and "lower haloalkane" as used herein refers to such compounds having from 5 to 12 carbon atoms. The term "halo" as employed herein refers to the substitution of one or more atoms of bromo, chloro or fluoro.

The amount of amine catalyst employed is that amount at which the amine will function effectively as a catalyst. In the practice of the present invention, the molar ratio of the phthalic anhydride to diethyl phosphoramidothioate is preferably between about 1 and about 4 and most preferably between about 2 and about 3. The ratio of the moles of amine catalyst to the combined moles of the reactants is preferably between about 0.5 and about 2, and most preferably between about 0.5 and about 0.75.

It is believed that the amine catalyst, especially the tertiary amine catalyst, behaves in the manner of a catalyst but further reacts with by-products of the reaction such that said by-products are removed from an active part in the reaction. Accordingly in the preferred mode of operating the method of this invention a sufficient quantity of catalyst is added to provide sufficient amine to effect complete reaction and remove all or substantially all the acidic by-products.

The reaction is generally carried out at a temperature in the range of about 20° to about 85° C. The preferred temperature range at atmospheric pressure is from about 45° C. to about 65° C. The reaction is preferably carried out at an ambient pressure but it can also be operated under elevated or reduced pressures.

When operating within the preferred conditions of temperature, pressure, and reactant and catalyst ratios, reaction times of from about 1 to about 6 hours are sufficient for practical completion.

The rate of addition and/or order of addition of the reactants phthalic anhydride and O,O-dialkyl phorphoramidothioate and the amine catalyst are not critical to the present process.

Upon completion of the reaction, the desired product phosphonothioate can be separated by treating the hot reaction mixture with an equal amount of hot water or acetone and stirring several minutes. The desired phosphonothioate can be filtered from the organic layer after the layer is cooled. The product can be further purified, if desired, by solvent recrystallization followed by drying. However, the specific mode of product separation is not critical and other conventional separatory procedures can be employed. An additional advantage of this invention is that the tertiary amine catalyst is recyclable and can be recovered from the aqueous mother liquor such as, for example, by treating the mother liquor with sodium hydroxide.

EXAMPLES

In order that the present invention may be more fully understood, the following examples are given primarily by way of illustration and should not be construed as limitations upon the overall scope of the present invention. Analysis of product wasy by gas-liquid chromatography (GLC) and high pressure liquid chromatography (HPLC), using internal standards.

EXAMPLE 1

A mixture of 92.5 g (0.625 moles) phthalic anhydride and 42.3 g (0.25 moles) O,O-diethylphosphoramidothioate in light petroleum (b.p 60°-80° C.) was stirred in a pressure bomb and then treated with 38 g (0.644 moles) of anhydrous trimethylamine. The temperature of the reaction medium was raised to 55° C. over 20 minutes and maintained thereat for 2½ hours. The bomb was opened and the system was treated with 200 ml of warm water and stirred for several minutes. The hot organic layer was cooled overnight to 0°-5° C. A solid was filtered and dried therefrom to give the desired compound, O,O-diethyl phthalimidophosphonothioate, which was analyzed at 88% purity by GLC. The yield of desired compound was calculated to be 20% from the O,O-diethylphosphoramidothioate.

EXAMPLE 2

A mixture of the 74.06 g (0.5 mole) phthalic anhydride, 33.84 g (0.2 mole) O,O-diethyl phosphoramidothioate and 50.60 g (0.5 mole) triethylamine was heated at 55° C. for 3.5 hours. Eighty three mls of water were added to the stirred mixture and the system was stirred for 10 minutes and then cooled to 25° C. over a one hour period. The solid was filtered, washed with 150 ml water to give the desired compound, O,O-diethyl phthalimidophosphonothioate, purity by GLC. The yield was calculated to be 76% from the phosphoramidothioate.

EXAMPLE 3

A mixture of 103.7 g (0.7 mole) phthalic anhydride, 47.3 g (0.28 mole) O,O-diethyl phosphoramidothioate and 129.5 g (0.7 mole) tributylamine was stirred and heated at 55° C. for 3 hours. One hundred and thirty three mls of water were added to the mixture and the resulting solution was cooled. No solid precipitated but the solution was shown by GLC analysis to contain the desired compound, O,O-diethyl phthalimidophosphonothioate, in 20% yield from the O,O-diethyl phosphoramidothioate.

EXAMPLE 4

A mixture of 222 g (1.5 moles) phthalic anhydride, 84.5 g (0.5 moles) O,O-diethyl phosphoramidothioate and 151 g (1.5 moles) triethylamine in 800 mls light petroleum (bP 60°-80° C.) was stirred and heated at 67° C. for 5.75 hours. Two hundred and eighty mls of water were added to the vigourously stirred system. After several minutes the mixture was allowed to stand and the hot organic layer was separated and cooled to 0°-5° C. to give the desired compound, O,O-diethyl phthalimidophosphonothioate, as a colorless solid, m.p. 75°-81° C. (97.5 purity by GLC). The yield was calculated to be 55% from the O,O-diethyl phosphoramidothioate. A further 4% yield of the desired compound was obtained by filtering the cooled aqueous layer.

EXAMPLE 5

A mixture of 148 g (1.0 mole) phthalic anahydride, 67.6 g (0.4 mole) O,O-diethyl phosphoramidothioate and 113 g (1.0 mole) N-ethylpiperidine was heated at 55° C. for 3.5 hours. One hundred and ninety mls of water at 35° C. were added to the stirred mixture and the system was stirred for 5 minutes and then allowed to cool to ambient temperature. The solid was filtered, washed with 25 ml water to give the desired compound, O,O-diethyl phthalimidophosphonothioate, analyzed at 94% purity by GLC. The yield was calculated to be 57% from the phosphoramidothioate.

Comparative Example

In a comparative run in which a tertiary amine catalyst was not utilized, a mixture of 148 g (1.0 moles) phthalic anhydride and 67.6 g (0.4 moles) O,O-diethyl phosphoramidothioate was stirred and heated at 55° C. for three hours. One hundred and ninety mls of water were added to the mixture. Analysis by GLC on the filtered solid indicated that no Product Compound was formed.

O,O-diethyl phosphoramidothioate is a known compound and is available commercially. It may be prepared by methods known to those skilled in the art, such as by reacting a phosphorochloridate of the formula $(C_2H_5O)_2P(S)Cl$ with $NH_3$, preferably in the presence of a hydrogen halide acceptor. Other O,O-dialkyl phosphoramidothioate starting materials may be prepared by methods known to those skilled in the art.

The phosphorochloridate which is utilized to prepare O,O-diethyl phosphoramidothioate may be prepared by reacting $Cl_3$—P=S successively (in either order) or simultaneously with a compound of the formula $C_2H_5O$-alkali metal as, for example, in the manner taught in U.S. Pat. No. 3,399,213. Phthalic anhydride is a well known compound and is available commercially.

Those who intend to practice this invention should note that phthalic anhydride is moderately toxic and a skin irritant and safety precautions whould be employed when handling same. O,O-diethyl phthalimidophosphonothioate exhibits a low degree of toxicity when compared with organo-phosphorus compounds in general. However, it is a skin irritant and therefore should be handled with caution. O,O-diethyl phosphoramidothioate and tertiary amine catalysts should also be handled with caution.

What we claim is:

1. A method of preparing a compound of the formula

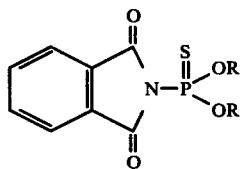

which method comprises reacting a phthalic anhydride with a compound of the formula

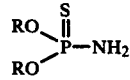

in the presence of an effective catalytic amount of at least one tertiary amine, said amine being an aliphatic tertiary amine of the formula $NR_3$ or a cyclic tertiary amine of the formula $(CH_2)_n$ N—R where n is 4, 5 or 6, wherein, in all of the above formulas each R substituent is, individually, an alkyl group having from 1 to 4 carbon atoms, thereby to produce a dialkyl phthalimidophosphonothioate.

2. The method of claim 1, wherein the catalyst is N-ethylpiperidine.

3. The method of claim 1, wherein the catalyst is triethylamine.

4. The method of claim 1, wherein the phthalic anhydride is unsubstituted.

5. A method of preparing O,O-diethyl phthalimidophosphonothioate which comprises reacting O,O-diethyl phosphoramidothioate with unsubstituted phthalic anhydride in the presence of an effective catalytic amount of a tertiary amine of the formula $NR_3$ wherein each R substituent individually represents a $C_1$-$C_4$ alkyl group, thereby to produce diethyl phthalimidephosphonothioate.

6. The method of claim 5 wherein the reaction temperature ranges from about 20° to about 85° C.

7. The method of claim 6, wherein the reaction temperature ranges from about 45° to about 65° C.

8. The method of claim 5, wherein the mole ratio of phthalic anhydride to O,O-diethyl phosphoramidothioate is from about 1 to about 4.

9. The method of claim 5, wherein the mole ratio of phthalic anhydride to O,O-diethyl phosphoramidothioate is from about 2 to about 3.

10. The method of claim 5, wherein the reaction time is from about 1 to about 6 hours.

11. The method of claim 5, wherein the reaction is run in the presence of a solvent selected from the group consisting of cyclohexane, decane and dichloroethane.

12. The method of claim 11, wherein the solvent is hexane.

13. The method of claim 5, wherein the tertiary amine is triethylamine.

14. The method of claim 13, wherein the ratio of the moles of triethylamine to the combined moles of O,O-diethyl phosphoramidothioate and phthalic anhydride is from about 0.5 to about 2.

15. The method of claim 8, wherein the ratio of the moles of triethylamine to the combined moles of O,O-diethyl phosphoramidothioate and phthalic anhydride is from about 0.5 to about 0.75.

* * * * *